United States Patent
Lal et al.

(10) Patent No.: US 9,321,881 B2
(45) Date of Patent: Apr. 26, 2016

(54) LIQUID METHYLENEDIANILINE COMPOSITIONS

(75) Inventors: Gauri Sankar Lal, Whitehall, PA (US); Kristen Elaine Minnich, Germansville, PA (US); Pritesh G. Patel, Breinigsville, PA (US); Gamini Ananda Vedage, Bethlehem, PA (US); Garret C. Lau, Emmaus, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 402 days.

(21) Appl. No.: 13/208,449

(22) Filed: Aug. 12, 2011

(65) Prior Publication Data
US 2013/0040060 A1 Feb. 14, 2013

(51) Int. Cl.
| | | |
|---|---|---|
| C08G 59/50 | (2006.01) |
| C07C 211/46 | (2006.01) |
| C07C 211/55 | (2006.01) |
| C09K 3/00 | (2006.01) |
| B05D 3/00 | (2006.01) |

(52) U.S. Cl.
CPC .......... *C08G 59/5033* (2013.01); *C07C 211/46* (2013.01); *C07C 211/55* (2013.01); *C09K 3/00* (2013.01)

(58) Field of Classification Search
None
See application file for complete search history.

(56) References Cited

U.S. PATENT DOCUMENTS

| | | | |
|---|---|---|---|
| 3,427,282 A * | 2/1969 | Sundholm | 528/124 |
| 3,634,275 A | 1/1972 | Sunholdm | |
| 3,825,598 A * | 7/1974 | Eifler et al. | 564/331 |
| 4,087,459 A * | 5/1978 | Knofel et al. | 564/331 |
| 4,259,526 A * | 3/1981 | Dunlap et al. | 564/331 |
| 4,303,773 A | 12/1981 | Ganster et al. | |
| 4,367,299 A * | 1/1983 | Renner et al. | 523/457 |
| 4,978,791 A * | 12/1990 | Volker et al. | 564/335 |
| 5,015,718 A | 5/1991 | Dorsey | |

FOREIGN PATENT DOCUMENTS

| | | |
|---|---|---|
| JP | 4731961 | 11/1972 |
| JP | S4731961 | 11/1972 |
| JP | 4885700 | 11/1973 |
| JP | S4885700 | 11/1973 |
| JP | 50-009839 | 4/1975 |
| JP | 50-009839 B | 4/1975 |
| JP | 2004359672 | 12/2004 |
| NL | 7 311 283 A | 2/1975 |
| NL | 7311283 | 2/1975 |

OTHER PUBLICATIONS

Y. Tanaka, Synthesis and Characteristics of Epoxides, Epoxy Resins Chemistry and Technology (Marcel Dekker), 1988.

(Continued)

*Primary Examiner* — Joseph D Anthony
(74) *Attorney, Agent, or Firm* — Michael K. Boyer

(57) ABSTRACT

A liquid methylenedianiline product is disclosed. The product is produced by reacting aniline and ethylaniline with formaldehyde with an amine to formaldehyde ratio greater than about 2:1. The resulting reaction product is a liquid mixture of methylenedianiline, monoethyl methylenedianiline, and diethyl methylenedianiline having a viscosity of less than about 1000 cps at 40° C.

23 Claims, 1 Drawing Sheet

(56) References Cited

OTHER PUBLICATIONS

H. Chen, et al, Studies on Low-Melting Point Aromatic Amine Hardener for Epoxy Resin I. Blend of DEDDM, MEDDM and DDM, Department of High Molecular Materials, East China University of Science and Technology, 1995, Shanghai.

* cited by examiner

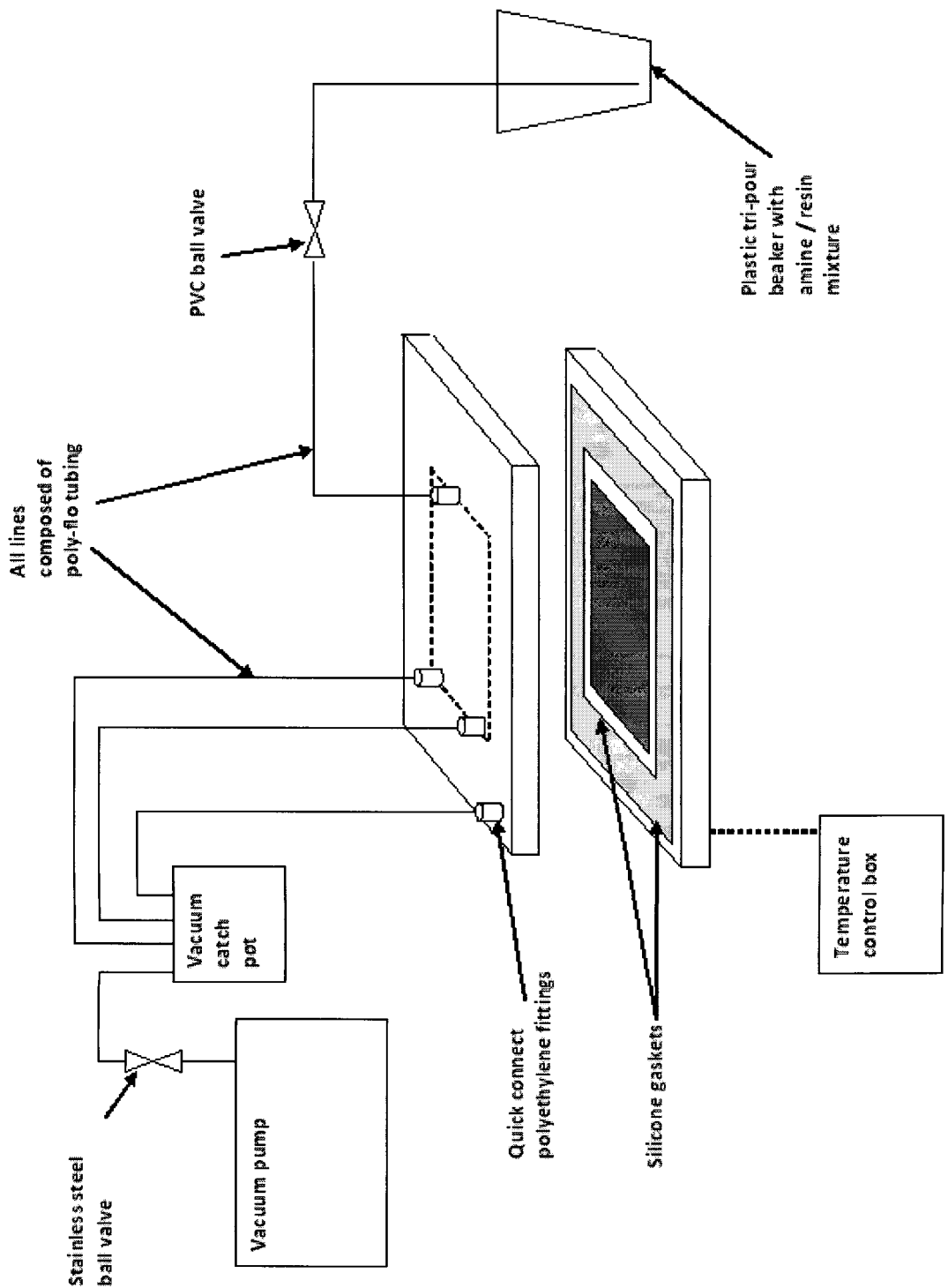

LIQUID METHYLENEDIANILINE COMPOSITIONS

FIELD OF THE INVENTION

The present invention is directed to compositions containing methylenedianiline and more particularly to such compositions in which the methylenedianiline is present in liquid form.

BACKGROUND OF THE INVENTION

A variety of 4,4'-methylenedianiline (MDA) based products are available. These compounds are useful as epoxy curing agents for applications in composite materials. However, MDA is generally solid at room temperature. As a result, the MDA is usually blended with toluene diamine (TDA), which dissolves the solid MDA and produces a liquid product that allows for easier processing. While these additives enhance the ability to process the MDA and use it as an epoxy curing agent as part of a blended mixture, such blends are still unsatisfactory because they tend to crystallize at low temperatures, which can result in premature gelation or resolidification during storage. Furthermore, these MDA/TDA blends result in formation of colored bodies during storage and cause extensive staining of manufacturing plants when in use.

The Dutch patent publication NL 7311283(A) exemplifies a diamine curing agent for epoxies in liquid form made from o-ethylaniline, aniline, formaldehyde and HCl. Similarly, Japanese Publication JP 50-009839(B) also exemplifies a liquid diamine from aniline, o-ethylaniline, formaldehyde and HCl. In each case, the molar ratio of amines to formaldehydes was 2:1, with the resulting product a composition including MDA in liquid form. These products can still be unsuitable as an epoxy curing agent in commercial environments because of their high viscosity, which were taught to be 1100 centipoise and which have been observed to be even higher.

MDA compositions not suffering from the above drawbacks would be desirable in the art.

BRIEF DESCRIPTION OF THE INVENTION

Exemplary embodiments are directed to a liquid methylenedianiline composition, a product that may be useful as an amine curing agent. The product is produced by reacting aniline and ethylaniline with formaldehyde, with an amine to formaldehyde ratio greater than 2:1. The resulting reaction product is a liquid mixture of methylenedianiline, monoethyl methylenedianiline, and diethyl methylenedianiline having a viscosity of less than about 1000 cps at 40° C.

In an exemplary embodiment, a composition comprises about 10% to about 25% by weight methylenedianiline, about 39% to about 43% by weight monoethyl methylenedianiline; and about 19% to about 41% by weight diethyl methylenedianiline. The composition is a liquid having a viscosity of less than about 1000 cps at 40° C.

In one exemplary embodiment, a composition consists essentially of methylenedianiline, monoethyl methylenedianiline, diethyl methylenedianiline and amine oligomers in which the composition is a liquid having a viscosity of less than about 1000 cps at 40° C. "Consisting essentially of" is intended to exclude components and materials in an amount that can increase the viscosity of the composition to greater than about 1000 cps.

According to another exemplary embodiment, a method of making an amine curing composition comprises providing a mixture of aniline and ethyl aniline and reacting the mixture of aniline and ethyl aniline with formaldehyde in which the molar ratio of amine groups to formaldehyde groups is greater than about 2:1.

According to yet another exemplary embodiment, a method of manufacturing an article comprises providing a composition that is a liquid mixture of methylenedianiline, monoethyl methylenedianiline, and diethyl methylenedianiline having a viscosity of less than about 1000 cps at 40° C. and providing an epoxy resin. The composition and the epoxy resin are combined to form a curable mixture which is applied to an article and cured. In some embodiments, the article is a composite material.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWING

FIG. 1 schematically illustrates a system for the fabrication of composite panels using an amine curing agent in accordance with exemplary embodiments.

Wherever possible, the same reference numbers will be used throughout the drawings to represent the same parts.

DETAILED DESCRIPTION OF THE INVENTION

Compositions in accordance with exemplary embodiments are low viscosity liquid aromatic amine compositions that can be used as curing agents and allow for easier processing when combined with an epoxy resin for application. These compositions do not require the presence of toluene diamine (TDA) or other solvents and can lessen or eliminate the problems of color formation and staining found in current liquid blends of methylenedianiline (MDA) and TDA and, in one aspect of the invention, the compositions can be substantially free of TDA. By "substantially free" it is meant that the composition includes less than about 5 wt. % TDA and, in some cases, about 0 wt. % TDA. They can also be used to produce epoxy coatings having more robust chemical resistance than those manufactured using known amine curing agents. Exemplary embodiments also demonstrate lower heats of reaction, better stiffness, and can remain liquid for at least a week, providing greater shelf life.

Exemplary embodiments are directed to liquid MDA compositions formed by the reaction of aniline and ethyl aniline, particularly ortho-ethyl aniline, with formaldehyde. The molar ratio of amines to formaldehyde in the reactant mixture is greater than 2:1, preferably greater than 3:1 and more preferably about 4:1. Increasing the molar ratio of amines to formaldehyde unexpectedly resulted in a reaction product having low viscosity.

The molar ratio of aniline to ethyl aniline in the reactant mixture may be about 50:50 or greater, such that the number of moles of aniline present is equal to and preferably greater than the number of moles of ethyl aniline. In one embodiment, the molar ratio of aniline to ethyl aniline is about 70:30. It is preferred to reduce the amount of ethyl aniline employed because it is expensive to produce and obtain, but without reducing the amount such that the reaction product no longer has a low viscosity.

The reaction by which compositions in accordance with exemplary embodiments may be achieved proceeds primarily according to the following schematic:

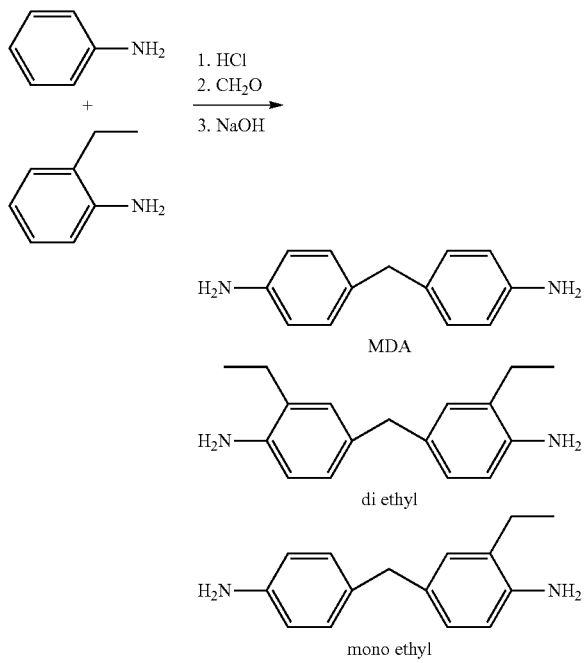

It will be appreciated that MDA is formed by the reaction of two aniline molecules, monoethyl MDA is formed by the reaction of aniline and ethyl aniline molecules, while diethyl MDA is formed by the reaction of two ethyl aniline molecules. The ethyl aniline is ortho-ethyl aniline and has a greater reactivity than aniline. As a result, despite the molar excess of aniline, the reaction products tend to favor the production of compounds containing at least one ethyl branch, i.e. monoethyl MDA and diethyl MDA, over MDA. In some embodiments, the reaction product formed in accordance with exemplary embodiments following separation from excess reactants may include about 10-25% wt. MDA, about 39-43% wt. monoethyl MDA, about 19-41% wt. diethyl MDA, with the balance being primarily oligomers of aniline and ethyl aniline with formaldehyde.

Exemplary embodiments yield a MDA composition as a reaction product that is liquid at room temperature and has a viscosity less than about 1000 cps, preferably less than about 750 cps, and more preferably in the range of about 300 to about 500 cps at temperatures of 40° C. or less.

The reaction may be carried out by combining the reactants with an aqueous solution of an acid catalyst. The acid catalyst may be any suitable acid and is typically a strong acid, such as HCl. The concentration of the acid in solution typically ranges from about 1 to about 37 wt. %; The amount of acid solution used in the reaction typically ranges from about 10 to about 40 wt. %. The reaction may be initiated and/or the rate of reaction increased by carrying out the reaction at elevated temperatures (e.g., in excess of 90° C.). The reaction may also be carried out under stirring conditions for more intimate contact of the organic and aqueous phases and to prevent separation. The reaction may also be carried out in the presence of an inert gas such as nitrogen blanketing.

After the reaction has reached equilibrium, the mixture may be cooled, followed by the introduction of an aqueous solution of a base to neutralize the acid. A strong base, such as NaOH, may be added to neutralize a strong acid catalyst.

The post-reaction mixture includes the reaction products, along with excess reactants including aniline and ethyl aniline, in an organic phase. An aqueous phase is also present. Separation may occur using any techniques known in the art. For example, the organic layer may first be separated from the aqueous layer, followed by distillation to remove any excess reactants that remain in the organic phase.

Following separation, a liquid MDA composition is achieved that consists essentially of MDA, monoethyl MDA, diethyl MDA, along with amine oligomers with formaldehyde as a byproduct. Small amounts of other reactants or byproduct constituents may be present following separation, provided those materials are present in amounts that do not adversely affect the composition's low viscosity or other advantages achieved with exemplary embodiments.

Compositions in accordance with exemplary embodiments can be employed as amine curing agents and used in combination with epoxy resins for the production of composites, motor windings and the like, or any other article in which a cured epoxy coating may be employed. MDA compositions in accordance with exemplary embodiments are non-staining according to measurement with ASTM D1544-04 (2010), Standard Test Method for Color of Transparent Liquids (Gardner Color Scale). Furthermore, the color of MDA compositions remains unchanged for about 60 days at room temperature. The low viscosity of exemplary embodiments at low temperatures can also eliminate the current practice of a preheated resin bath used in traditional filament winding processes. This results in energy savings during manufacturing. The ratio of inventive amine curing agents to epoxy typically ranges from about 5 to about 50:100.

Exemplary embodiments further contribute to improved fiber wetting, leading to a more consistent product. These fibers (wovens or non-wovens) can be coated with epoxy resin mixtures using amine curing agents as described herein by standard impregnating methods and may be used with filament winding, pultrusion, sheet molding compound, bulk molding compound, autoclave molding, resin infusion, vacuum assisted resin transfer molding, hand lay-up, resin impregnation, prepreg, compression molding, brushing, spraying, dipping, casting, injection molding or combinations thereof.

The amine curing agent described herein can be used to form curable epoxy resin compositions and cured products such as adhesives, structural and electrical laminates, coating, casting, structural components for aerospace industries, and as circuit boards and the like for the electronics industry, among other applications. Other uses may include electrical varnishes, encapsulants, semiconductors, general molding powders, filament wound pipe, storage tanks, liners for pumps, and corrosion resistant coatings, and other suitable epoxy containing products.

Amine curing agents in accordance with exemplary embodiments can be used as a curing agent for any suitable epoxy resin and may be used, for example, with the epoxy resins commercially available under the trade name DER 383 (available from Dow) and EPON 826 (available from Hexion Specialty Chemicals).

Other epoxy resins may include, but are not limited to, bi-functional epoxies, such as, bisphenol-A and bisphenol-F resins. Multifunctional epoxy resin, as utilized herein, describes compounds containing two or more 1,2-epoxy groups per molecule. Epoxide compounds of this type are well known to those of skill in the art and are described in Y. Tanaka, "Synthesis and Characteristics of Epoxides", in C. A.

May, ed., Epoxy Resins Chemistry and Technology (Marcel Dekker, 1988), which is incorporated herein by reference.

One class of epoxy resins suitable for use in the present disclosure comprises the glycidyl ethers of polyhydric phenols, including the glycidyl ethers of dihydric phenols. Illustrative examples include, but are not limited to, the glycidyl ethers of resorcinol, hydroquinone, bis-(4-hydroxy-3,5-difluorophenyl)-methane, 1,1-bis-(4-hydroxyphenyl)-ethane, 2,2-bis-(4-hydroxy-3-methylphenyl)-propane, 2,2-bis-(4-hydroxy-3,5-dichlorophenyl)propane, 2,2-bis-(4-hydroxyphenyl)-propane (commercially known as bisphenol A), bis-(4-hydroxyphenyl)-methane (commercially known as bisphenol-F, and which may contain varying amounts of 2-hydroxyphenyl isomers), and the like, or any combination thereof. Additionally, advanced dihydric phenols of the following structure also are useful in the present disclosure:

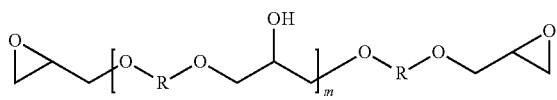

where m is an integer, and R is a divalent hydrocarbon radical of a dihydric phenol, such as those dihydric phenols listed above. Materials according to this formula can be prepared by polymerizing mixtures of a dihydric phenol and epichlorohydrin, or by advancing a mixture of a diglycidyl ether of the dihydric phenol and the dihydric phenol. While in any given molecule the value of m is an integer, the materials are invariably mixtures which can be characterized by an average value of m which is not necessarily a whole number. Polymeric materials with an average value of m between 0 and about 7 can be used in one aspect of the present disclosure. In other embodiments, the epoxy component may be a polyglycidyl amine from one or more of 2,2'-methylene dianiline, m-xylene dianiline, hydantoin, and isocyanate.

The epoxy component may be a cycloaliphatic (alicyclic) epoxide. Examples of suitable cycloaliphatic epoxides include diepoxides of cycloaliphatic esters of dicarboxylic acids such as bis(3,4-epoxycyclohexylmethyl)oxalate, bis(3,4-epoxycyclohexylmethyl)adipate, bis(3,4-epoxy-6-methylcyclohexylmethyl)adipate, vinylcyclohexene diepoxides; limonene diepoxide; bis(3,4-epoxycyclohexylmethyl)pimelate; dicyclopentadiene diepoxide; and other suitable cycloaliphatic epoxides. Other suitable diepoxides of cycloaliphatic esters of dicarboxylic acids are described, for example, in WO 2009/089145 A1, which is hereby incorporated by reference.

Other cycloaliphatic epoxides include 3,3-epoxycyclohexylmethyl-3,4-epoxycyclohexane carboxylate such as 3,4-epoxycyclohexylmethyl-3,4-epoxycyclohexane carboxylate; 3,3-epoxy-1-methylcyclohexyl-methyl-3,4-epoxy-1-methylcyclohexane carboxylate; 6-methyl-3,4-epoxycyclohexylmethylmethyl-6-methyl-3,4-epoxycyclohexane carboxylate; 3,4-epoxy-2-methylcyclohexyl-methyl-3,4-epoxy-3-methylcyclohexane carboxylate. Other suitable 3,4-epoxycyclohexylmentyl-3,4-epoxycyclohexane carboxylates are described, for example, in U.S. Pat. No. 2,890,194, which is hereby incorporated by reference. In other embodiments, the epoxy component may include polyol polyglycidyl ether from polyethylene glycol, polypropylene glycol or polytetrahydrofuran or combinations thereof.

EXAMPLES

The invention is further described in the context of the following examples, which are presented by way of illustration, not of limitation.

Example 1

Aniline (23.2 g) and ortho-ethyl aniline (30.3 g) were stirred in a round-bottomed flask fitted with an overhead stirrer, $N_2$ blanket and addition funnel. A mixture of water (22.5 g) and HCl (12.32 g, 37%) was added dropwise, keeping the temperature at approximately 40° C. After that mixture was completely added, the flask contents were stirred for 30 minutes. Formaldehyde (10.15 g, 37% in water) was then added dropwise over a 20 minute period. The reactants were heated to 90° C. and that temperature was maintained for 2.5 hours while the reaction proceeded. After that period elapsed, the flask contents were cooled to 30° C. NaOH (11.01 g, 50% in water) was then added dropwise and the flask contents stirred for an additional 30 minutes.

After stirring was finished, the contents separated into aqueous and organic layers. The aqueous layer was removed and the remaining organic layer was rinsed three times with water. Excess amine and residual water were then removed by vacuum distillation, leaving a low viscosity liquid that was subsequently characterized by further testing.

Example 2

A composition was prepared as described in Example 1, except that the amine starting materials were 30.3 g aniline and 21.2 g ortho-ethyl aniline.

Example 3

A composition was prepared as described in Example 1, except that the amine starting materials were 32.6 g aniline and 18.2 g ortho-ethyl aniline.

Comparative Example 1

A first comparative example was prepared using a 2:1 molar ratio of amine to formaldehyde as taught and exemplified in NL 7311283(A) and JP 50-009839(B), although the aniline to ortho-ethyl aniline molar ratio was higher in this comparative example. Comparative Example 1 was prepared as described in Example 1, except that the amine starting materials were 19.8 g aniline and 4.5 g ortho-ethyl aniline.

Table 1 illustrates a summary of the molar feed ratio of amine to formaldehyde groups, as well as aniline to ortho-ethyl aniline for each of Examples 1-3 and Comparative Example 1. In each case the resulting composition of the reaction was a liquid. Table 1 further includes the weight percentages of each of the reaction products, as determined by gas chromatography, including MDA, mono ethyl MDA ("Mono Et MDA") and diethyl MDA ("Di Et MDA"), as well as oligomeric by-products (grouped collectively).

TABLE 1

| Example | Molar Feed Ratio Amine/CH$_2$O | Molar Feed Ratio (%) Aniline | Et Aniline | Reaction Products in Weight % (as determined by GC) |  |  | Oligomers |
|---|---|---|---|---|---|---|---|
| | | | | MDA | Mono Et MDA | Di Et MDA | |
| 1 | 4:1 | 50 | 50 | 10 | 39 | 41 | 10 |
| 2 | 4:1 | 65 | 35 | 21 | 43 | 22 | 14 |
| 3 | 4:1 | 70 | 30 | 25 | 43 | 19 | 13 |
| Comparative 1 | 2:1 | 85 | 15 | 46 | 24 | 2 | 28 |

Example 4

The amine curing compositions made according to Examples 1-3 and Comparative Example 1 were used for curing epoxy resins. The commercial epoxy resin EPON 826 (available from Hexion Specialty Chemicals) was cured with a stoichiometric amount of various inventive and comparative curing agents, including two additional commercially available amine curing agents designated as Comparative Examples 2 and 3, both of which were types of eutectic amines available from Air Products under the tradename ANCAMINE®. ANCAMINE® is a registered trademark of Air Products and Chemicals, Inc.

The cured epoxy compounds formed using each of the amine curing agents are reflected in Table 2, including mixture formulation and the resulting physical properties. The viscosity of the neat amine curative composition and the curative/epoxy mixture formulation viscosity were obtained at 40° C. and 60° C. respectively.

TABLE 2

| | Comparative Ex. 1 | Comparative Ex. 2 | Comparative Ex. 3 | Example 3 |
|---|---|---|---|---|
| Eq. Weight | 54 | 51 | 48 | 56 |
| Amine Value (mg KOH/g) | 520 | 555 | 620 | 508 |
| Neat Amine Curing Agent Viscosity @40° C. (cps) | 3000 (under ideal conditions) | 45,000 | 1,200 (under ideal conditions) | 450 |
| Curing Agent in Formulation with EPON 826 resin (phr) | 30 | 28 | 27 | 31 |
| Formulation Viscosity @60° C. (cps) | 235 | 335 | 235 | 155 |

Additional studies also reflected that MDA compositions in accordance with exemplary embodiments remained liquid regardless of weathering conditions to which the samples were subjected, and remained liquid even after exposure to 0° C. for 48 hours and did not exhibit signs of initiating crystallization as seen with currently available eutectic amine curing agents when exposed to those temperatures.

Example 5

The reactivity of the epoxy/curing agent mixtures formulated in Example 4 was measured at 60° C. using a Brookfield viscometer using a #27 spindle. A Techne gelation timer was used to measure the gel time of those mixtures.

In each case, stoichiometric amounts of epoxy resin and curing agent were preheated separately at 90° C. for 60 minutes. The epoxy and curing agent were then mixed together for a period of between 3 to 5 minutes. In each case, 60 g of the epoxy/curative mixture was next poured into a 100 ml glass beaker mounted in a silicon oil bath set at 90° C.

Reactivity results are shown in the Table 3.

TABLE 3

| | Comparative Ex. 1 | Comparative Ex. 2 | Comparative Ex. 3 | Example 3 |
|---|---|---|---|---|
| Time to 10,000 cps @60 C. (hours) | 229 | 193 | 216 | 311 |
| Gel time @90 C. (hours) | 43 | 24 | 29 | 56 |
| DSC Reactivity | | | | |
| Onset (° C.) | 77 | 75 | 77 | 90 |
| Peak (° C.) | 171 | 180 | 171 | 178 |
| ΔH (J/g) | 331 | 400 | 390 | 310 |
| Tg (° C.) | 160 | 160 | 160 | 150 |

It was observed that epoxies made using amine curing compositions in accordance with exemplary embodiments demonstrated a longer gel time than those using commercial curing agents when cured with the epoxy resins DER 383 and EPON 826 at 90° C. This corresponds to a longer pot life when exemplary embodiments are used as an amine curing agent and represents an advantage by decreasing the frequency of resin bath replenishment in industrial settings.

In addition, the heat of reaction (ΔH) or amount of exotherm developed during cure is lower for amine compositions in accordance with exemplary embodiments. This characteristic may permit a composite fabricator or other manufacturer to form a thicker part without burning or producing hot spots in the final product being fabricated.

Example 6

The polyepoxied and amine curatives described above in Example 4 were hand mixed at 40° C. for 3 to 5 minutes. In each case, entrapped air was removed by placing the mixture in a centrifuge for 5 minutes or until the mixture was clear. The mixture was then poured into a 1 inch by 3 inch by ⅛ inch mold. The mold was cured at 80° C. for 2 hours followed by 150° C. for an additional 3 hours. The molds were allowed to cool to room temperature and the ⅛ inch casting was removed. The cast samples were then prepared for mechanical testing. ASTM methods were used in this Example and subsequent Examples to test the samples to determine tensile strength (ASTM D638), flexural strength (ASTM D790) and compressive strength (ASTM D695).

Mechanical properties of the cast panel are reported in Table 4. Tensile and compressive properties of products using MDA compositions in accordance with exemplary embodiments were observed similar to the commercial products.

TABLE 4

|  | Comparative Ex. 1 | Comparative Ex. 2 | Comparative Ex. 3 | Example 3 |
| --- | --- | --- | --- | --- |
| Tensile Strength (MPa) | 70 | 65 | 82 | 75 |
| Tensile Modulus (GPa) | 2.8 | 2.94 | 2.8 | 2.96 |
| % Elongation | 4.0 | 3.5 | 5.0 | 5.0 |
| Flexural Strength (MPa) | 121 | 124 | 134 | 120 |
| Flexural Modulus (GPa) | 3.1 | 3.1 | 2.5 | 3.0 |
| Comp. Strength (MPa) | 125 | 121 | 119 | 123 |
| Comp. Modulus (GPa) | 2.0 | 1.8 | 2.1 | 1.9 |

Example 7

Additional samples were prepared in the same manner and immersed in various reagents for 120 days at 25° C. to perform chemical resistance testing with respect to Comparative Examples 2 and 3, the results of which are shown in Table 5. Overall, the chemical resistance results for MDA compositions in accordance with exemplary embodiments were generally as good or better than commercial eutectic amine curing agents.

TABLE 5

| % wt. Gain | Comparative Ex. 2 | Comparative Ex. 3 | Example 3 |
| --- | --- | --- | --- |
| DI water | 1.9 | 2.0 | 1.88 |
| Jet fuel C | 0.1 | 0.6 | 0.1 |
| Toluene | 0.2 | 0.2 | 0.01 |
| Acetone | 10.7 | 11.9 | 8.2 |
| Ethanol | 0.8 | 0.6 | 0.7 |
| Methanol | 8.97 | 10.5 | 7.8 |
| $HNO_3$ (20% by wt. aqueous solution) | 2.9 | 3.2 | 3.8 |
| Acetic Acid (25% by wt. aqueous solution) | 1.4 | 1.1 | 1.5 |

Example 8

Composite panels were fabricated using Vacuum Assisted Resin Transfer Molding (VARTM) as shown in the schematic of FIG. 1.

A metal mold was prepared by coating the entire mold inner surface with the mold release film SEALER GP followed by ENVIROSHIELD non-hazardous release agent, both available from Zyvax, to avoid sticking of epoxy with the mold's aluminum surface. The mold was heated to 45° C. for 30 minutes to ensure the release agent was completely dried before stacking glass fabric. Mold plates were machined to produce 6 inch×6 inch×⅛ inch (length×width×depth) composite panels. Twelve layers of unidirectional fiber glass (275 gram/meter$^2$) were carefully stacked into the mold cavity without fabric overlap or wrinkles in each layer. The top half of the mold was then closed while heating at 45° C. was continued. Tubing was connected and a rotary vacuum pump was used to evacuate the system down to approximately 15 psi (29 inch Hg), a level at which the vacuum was maintained.

Stoichiometric amounts of EPON 826 and the curing compositions used in Example 4 were hand mixed at 40° C. for 3 to 5 minutes. Entrapped air was removed by placing the mixture in a centrifuge for 5 minutes or until the mixture was clear. The mixture was placed next to the mold inlet tube and a PVC ball valve was gently opened to let the mixture flow through the tube to infuse the fiberglass plies layered within the closed aluminum mold.

The fibers were infused with resin until most of the mixture was consumed from the beaker; excess resin was collected in a catch pot. Integrated rod heaters allow the mold to be pre-warmed during infusion (40° C. to 60° C.) that allows a uniform flow of resin into the mold to enhance fiber wetting. The mold was cured at 80° C. for 2 hours followed by curing at 150° C. for 3 hours. After curing, the mold was cooled to room temperature prior to removing the composite panel. The resultant panels were each inspected to determine it was free from flaws. The panels were then used to prepare specimens for mechanical testing, the results of which are shown in Table 6.

TABLE 6

Mechanical Properties of composite panels

| Mechanical Properties | Comparative Ex. 1 | Comparative Ex. 2 | Comparative Ex. 3 | Example 3 |
| --- | --- | --- | --- | --- |
| Flexural Strength (MPa) | 1043 | 1066 | 1154 | 1140 |
| Flexural Modulus (GPa) | 47 | 47.4 | 50 | 47.5 |
| Interlaminar Shear Strength (ASTM D-2433) | 74.3 | 73.6 | 69.5 | 75.8 |

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A product made by a process comprising
   providing a mixture of aniline and ethyl aniline; and reacting the mixture of aniline and ethyl aniline with formaldehyde, wherein the molar ratio of amine groups to formaldehyde groups is greater than about 4:1 and the product consists essentially of:
   10 to 25 wt % methylenedianiline;
   39 to 43 wt. % monoethyl methylenedianiline;
   19 to 41 wt. % diethyl methylenedianiline; and the balance being oligomers of formaldehyde with aniline and ethyl aniline and wherein the product has a viscosity of less than about 750 cps at 40° C.

2. The product of claim 1 having a viscosity in the range of about 300 to about 500 cps at 40° C.

3. The product of claim 1 wherein the composition is non-staining as measured by the Gardner color scale.

4. The product of claim 1 wherein the composition is substantially free of toluene diamine.

5. The product of claim 1 wherein the composition comprises about 0 wt. % of toluene diamine.

6. The product of claim 1, wherein the molar ratio of aniline to ethyl aniline in the provided mixture is about 70:30.

7. The product of claim 1, wherein the molar ratio of aniline to ethyl aniline is at least about 50:50.

8. The product of claim 1, wherein the aniline and ethyl aniline are reacted with formaldehyde in the presence of an acid.

9. The product of claim 8, wherein the acid is present as an aqueous solution.

10. The product of claim 9, the process further comprising, after the step of reacting, separating from the mixture a liquid composition comprising methylenedianiline, monoethyl methylenedianiline, and diethyl methylenedianiline.

11. The product of claim 10, wherein the separated liquid composition comprises 10% to 25% by weight methylenedianiline; 39% to 43% by weight monoethyl methylenedianiline; and 19% to 41% by weight diethyl methylenedianiline.

12. The product of claim 10, wherein the separated liquid composition has a viscosity in the range of about 300 to about 500 cps at 40° C.

13. The product of claim 1 wherein the step of reacting is carried out at a temperature of about 90° C. or greater.

14. The product of claim 1 wherein the product comprises ethyl aniline.

15. The product of claim 14 wherein the product comprises aniline.

16. The product of claim 1 further comprising at least one epoxy resin comprising bisphenol-A.

17. The product of claim 1 further comprising at least one epoxy resin comprising glycidyl ethers or polyhydric phenols.

18. The product of claim 1 further comprising at least one epoxy resin comprising cycloaliphatic (alicyclic) epoxide.

19. The product of claim 16 wherein the process further comprises infusing the product into fiber glass.

20. The product of claim 1 further comprising at least one epoxy resin comprising bisphenol-A thereby producing a product having a viscosity at 60° C. of about 155 cps.

21. The product of claim 1 further comprising at least one epoxy resin comprising bisphenol-A thereby producing a product having a gel time at 90° C. of about 56 hours.

22. The product of claim 1 further comprising at least one epoxy resin comprising bisphenol-A and the process further comprises infusing the product into fiber glass.

23. The product of claim 6 wherein the product comprises about 25% by weight methylenedianiline; about 43% by weight monoethyl methylenedianiline; and about 19% by weight diethyl methylenedianiline.

\* \* \* \* \*